US00PP11587P

United States Patent [19]

Sherman

[11] Patent Number: Plant 11,587

[45] Date of Patent: Oct. 24, 2000

[54] NECTARINE TREE NAMED 'UFQUEEN'

[76] Inventor: Wayne B. Sherman, University of Florida, P.O. Box 110690, Gainesville, Fla. 32611-0690

[21] Appl. No.: 09/118,880

[22] Filed: Jul. 20, 1998

[51] Int. Cl.[7] ..... A01H 5/00

[52] U.S. Cl. ..... Plt./190

[58] Field of Search ..... Plt./190

[56] References Cited

U.S. PATENT DOCUMENTS

P.P. 5,461 5/1985 Zaiger ..... Plt./190

P.P. 7,402 12/1990 Zaiger et al. ..... Plt./190

*Primary Examiner*—Lynette R. F. Smith

*Assistant Examiner*—Wendy A Baker

[57] ABSTRACT

A new and distinct variety of nectarine tree which has a low winter chilling requirement of approximately 250 chill units (cu). The tree is of large size, is highly vigorous spreading growth habit and has nonshowy pink flowers. Glands are small and reniform in shape and isolated to the basal portions of leaves. This tree, which has been denominated 'UFQueen' is a regular bearer of heavy crops of early maturing, large for early ripening season, with very firm non-melting flesh, clingstone fruit having yellow flesh color. Fruit is uniform, attractive, substantially symmetrical shape, and has an attractive normally 90 to 100% solid red skin. The fruit ripens substantially with that of 'Sunraycer' in early to mid-May at Gainesville, Fla.

1 Drawing Sheet

BACKGROUND OF THE NEW VARIETY

The present invention relates to a new and distinct variety of nectarine (*Prunus persica* (L.) Batsch) tree which is named 'UFQueen' and, more particularly to a nectarine tree which produces highly colored, good eating quality, clingstone, non-melting flesh fruit which are mature for fresh market in early to mid-May at Gainesville and which are produced on a tree adapted to a mild winter climate. Asexual propagation was performed at Gainesville, Fla. where the selection was made and tested. Contrast is made to 'Sunraycer' (unpatented) nectarine, a standard variety, for reliable description. This new variety is a promising candidate for commercial success in that it retains fruit firmness at the full flavor, tree ripe stage for 10 days on the tree.

ORGIN OF THE VARIETY

This nectarine tree (genotype) originated in the tree fruit breeding program at the University of Florida, located at Gainesville, Fla. 'UFQueen' originated as an open-pollination of selection Fla.86-28c (unpatented), a non-melting flesh peach. 'UFQueen' nectarine was selected from about 80 siblings in 1994, and exhibited yellow, non-melting, clingstone flesh, and thus was designated Fla. 94-28cn. It was propagated asexually as a uniform variety and determined at Gainesville to have unique tree and fruit characteristics making it worthy for commercial production. 'UFQueen' has transmitted uniformity in fruit and tree traits through two standard asexual propagations by budding on 'Flordaguard' (unpatented) seedling rootstock. There are no known effects of 'Flordaguard' rootstock on the scion variety.

SUMMARY OF THE VARIETY

The new and distinct variety of nectarine tree bears yellow, non-melting flesh fruit, and has a low-chilling dormancy requirement. 'UFQueen' blooms with 'Sunraycer' nectarine at Gainesville and is the only nectarine variety known to me in the USA with such a low-chilling requirement that bears red skin over yellow and non-melting flesh, with early-ripening fruit. The estimated chilling requirement is 250 chill units. When grown in subtropical climates to take maximum advantage of its early bloom (low-chilling)

'UFQueen' will be among the first non-melting flesh nectarine varieties to ripen in the USA.

The present invention resulting in 'UFQueen' nectarine tree is characterized by non-melting flesh fruit of excellent flavor and eating quality on a tree adapted to mild winters. The trees are vigorous, productive and regular bearing. Trees attain in two years a height of three meters and a spread of two meters at Gainesville. Terminal growth of up to a meter is common on mature five-year-old trees. The first fruit ripen in early to mid-May at Gainesville or in about 95 days from full bloom. The fruit are uniformly medium large for an early ripening nectarine. Ripe fruit have 90 to 100 percentage of solid red skin color with no red pigment throughout the flesh or at the pit. The flower anthers are light red to yellow, a common characteristic of many standard nectarine and peach varieties.

BRIEF DESCRIPTION OF THE DRAWING

The accompanying color photograph shows a typical specimen of the fruit, leaf, and stem of the new variety as nearly true as it is reasonably possible to make in a color illustration of this type. The photograph shows an attractive shape and exterior coloration of four specimens of fruit above a ruler in side view, stem end view, a blossom end view, and side view showing the suture. It also depicts new wood, internode length, leaves, glands, leaf stems, and axillary buds.

BOTANICAL DESCRIPTION OF VARIETY

The tree, flowers, and fruit may vary in slight detail due to variations in soil type, cultural practices, and climatic condition. The potential for commercial production of fresh fruit by 'UFQueen' is high, due to its attractive red skin, early ripening of good flavor, and exceptional firmness due to its non-melting flesh. The present botanical description is that of the variety grown under the ecological conditions prevailing near Gainesville, Fla. Colors are described from "The Pantone Book of Color" published by H. N. Abrams, Inc., N.Y. 1990.

Tree:

*Size.*—Trees are normal and have been trained to an open vase form and are pruned in summer to keep center of vase open.

*Vigor.*—Vigorous, must be summer and winter pruned to keep tree height restricted and to keep center of vase open.

*Density.*—Medium to dense.

*Form.*—Semi-upright when pruned to vase shape.

*Bearer.*—Regular, must be fruit thinned to avoid limb breakage and obtain larger fruit size.

Trunk:

*Size.*—Medium, attaining 2 to 2½ inches (5 to 6.5cm) at 12 inches (30cm) above the ground on 2-year-old orchard trees.

*Texture.*—Medium smooth.

*Bark color.*—Older bark gray, Lead Gray (Pantone 17-1118).

*Lenticels.*—Numerous, small (2–4 mm), with the center being Mineral Yellow (Pantone 15-1046).

Branches:

*Size.*—Normal, strong, and in the range of standard varieties.

*Texture.*—Relatively smooth, medium amount of lenticels.

*Color.*—Young stems are light green, Tarragon (Pantone 15-0326).

*Crotch angles.*—Seleted at 45 to 90 degrees in first year of tree training. Natural angles are within the normal range of standard varieties for a semi-upright tree.

Leaves:

*Size.*—Medium; 15 to 19 cm length, including the petiole; 3 to 4 cm width. Measurements on vigorous upright shoots of summer growth.

*Thickness.*—Regular.

*Form.*—Lanceolate.

*Apex.*—Acute.

*Margin.*—Serrulate, slightly undulate.

*Base.*—Cuneate.

*Surface.*—Glabrous.

*Color.*—Lower dark green, Grasshopper (Pantone 18-0332); upper slightly darker green, Chive (Pantone 19-0323).

*Glands.*—Usually two, but occasionally four very small reniform glands mostly on lower leaf blade, but occasionally on petiole.

*Petiole.*—About 1 cm (0.7 to 1.1 cm).

*Stipules.*—Medium and early deciduous.

Flower buds:

*Abundance.*—Moderately high, mostly buds set fruit in absence of spring frosts.

*Size.*—Medium.

*Length.*—Medium.

*Shape.*—Plump, conic.

*Surface.*—Pubescent scales.

Flowers:

*Blossom period.*—With Sunraycer nectarine—average February 8–12th at Gainesille.

*Size.*—Non-showy, location and seasonally variable, but within the range of nonshowy varieties.

*Color.*—Pink, darkening to pink-red before abscising and within the range of standard varieties.

*Calyx cup.*—Medium small.

*Anthers.*—Light red to yellow, regular size.

*Pollen.*—Abundant and bright yellow (common to many varieties).

*Fertility.*—Self fertile.

Fruit:

*Maturity when described.*—Tree ripe, May 13, 1998 at Gainesville.

*Date of first picking.*—May 10, 1998 at Gainesville (normal).

*Date of last picking.*—May 19, 1998 at Gainesville (normal).

*Size.*—Uniform, medium large (large size for early maturity at 110 to 125 grams). Average equator diameter. — 2¼ inches (57 mm). Average polar length. (stem to distal end). — 2⅜ inches (60 mm).

Form:

*Longitudinal section form.*—Slightly oval.

*Transverse section through diameter.*—Round.

*Suture.*—Shallow and inconspicuous.

*Ventral surface.*—Rounded.

*Base.*—Slightly retuse.

*Cavity.*—Flaring circular.

*Depth.*—¼ to ⅜ inch (6 to 9 mm).

*Breadth.*—5/32 inch (3 mm).

Skin:

*Thickness.*—Medium.

*Texture.*—Medium.

*Tenacity.*—Tenacious to flesh.

*Color.*—Red, Garnet (Pantone 19-1655) over 90 to 100% of skin. Ground color is yellow, Saffron (Pantone 14-1064).

*Tendency to crack.*—None observed.

Flesh:

*Ripens.*—Evenly.

*Texture.*—Firm, juicy, non-melieg when fully ripe.

*Fibers.*—Very fine, tender, small.

*Aroma.*—High.

*Eating quality.*—good, sweet, subacid.

*Juice.*—Abundant.

*Color.*—Deep, yellow, Daffodil (Pantone 14-0850) with no redness throughout the flesh or at pit.

*Browning by oxidation.*—Slight on soft ripe fruit.

Stone:

*Type.*—Clingstone, adhering to flesh even at softening.

*Size.*—Medium small; average length — 30 mm, average width — 23 mm.

*Color.*—Brown, Buckskin (Pantone 16-1342) when freshly exposed.

*Form.*—Oblong.

*Base.*—Straight.

*Apex.*—Acute.

*Sides.*—Equal.

*Surface.*—Irregularly farrowed toward the ventral edge.

*Ridges.*—Jagged toward the base.

*Pit wall.*—3/16 to ¼ inch thick (5 to 6 mm).

*Tendency to split.*—None observed.

*Use.*—Fresh; dessert.

*Resistance to disease.*—High resistance to bacterial spot incited by *Xanthomonas campestris*. Resistance to other fruit and tree diseases are within the range for commercial peach cultivars in Florida.

*Keeping quality.*—Excellent.

*Shipping quality.*—Degree of firmness at harvest and firmness retained in refrigeration at 7C for 2 weeks indicates fruit should be highly acceptable for shipping.

We claim:

1. A new and distinct nectarine tree variety as illustrated and described, characterized by a low- chillimg requirement and bearing early-ripening fruit with firm, yellow, non-melting flesh and high eating quality and an attractive high percentage red over color with fruit ripening in early to mid-May or with 'Sunraycer' at Gainesville.

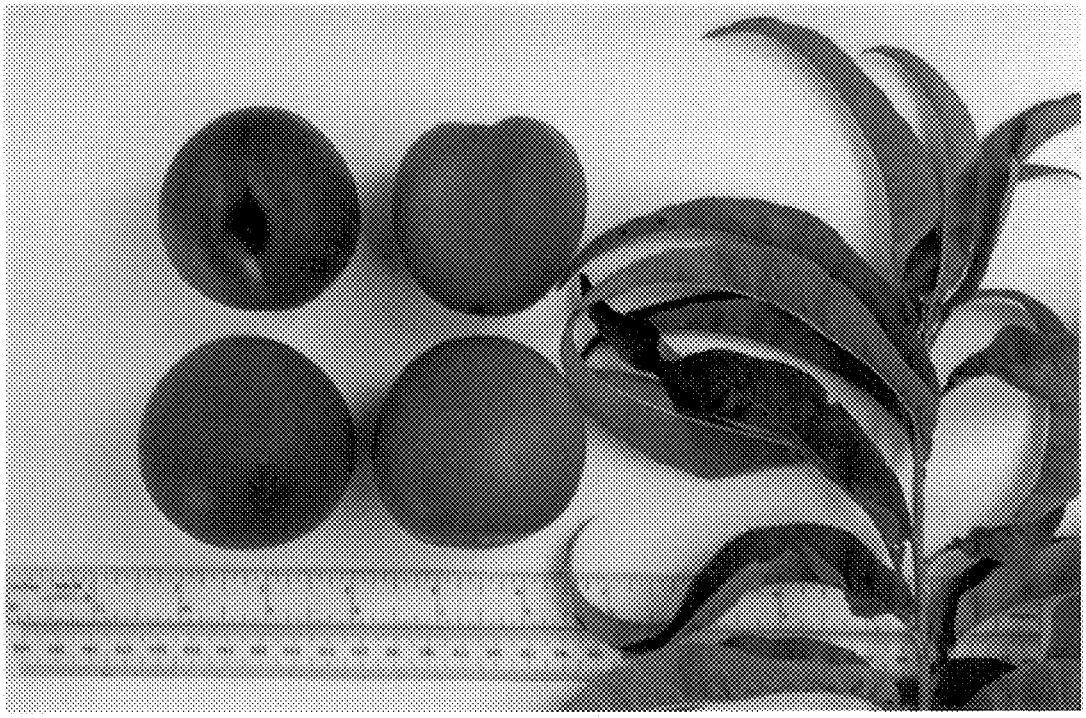

* * * * *